(12) United States Patent
Maier

(10) Patent No.: US 9,149,442 B2
(45) Date of Patent: Oct. 6, 2015

(54) TRANSDERMAL THERAPEUTIC SYSTEM CONTAINING ELONGATE HOLLOW BODIES

(75) Inventor: Stephan Maier, Leverkusen (DE)

(73) Assignee: LTS Lohmann Therapie-Systeme AG, Andernach (DE)

(*) Notice: Subject to any disclaimer, the term of this patent is extended or adjusted under 35 U.S.C. 154(b) by 582 days.

(21) Appl. No.: 12/675,827

(22) PCT Filed: Aug. 16, 2008

(86) PCT No.: PCT/EP2008/006742
§ 371 (c)(1),
(2), (4) Date: Mar. 1, 2010

(87) PCT Pub. No.: WO2009/030351
PCT Pub. Date: Mar. 12, 2009

(65) Prior Publication Data
US 2010/0303892 A1    Dec. 2, 2010

(30) Foreign Application Priority Data
Aug. 29, 2007 (DE) .......................... 10 2007 041 557

(51) Int. Cl.
*A61K 9/70* (2006.01)
*A61K 47/00* (2006.01)
*A61K 9/00* (2006.01)

(52) U.S. Cl.
CPC ............... *A61K 9/703* (2013.01); *A61K 9/0092* (2013.01); *A61K 9/7092* (2013.01)

(58) Field of Classification Search
CPC ....... A61K 9/0092; A61K 9/703; A61K 9/70; A61K 9/7023
USPC .......................... 424/449, 443, 448
See application file for complete search history.

(56) References Cited

U.S. PATENT DOCUMENTS

| 4,801,458 A * | 1/1989 | Hidaka et al. ................. 424/443 |
| 5,149,538 A * | 9/1992 | Granger et al. ............... 424/449 |
| 6,231,885 B1 * | 5/2001 | Carrara ......................... 424/448 |
| 6,719,997 B2 * | 4/2004 | Hsu et al. ...................... 424/443 |
| 2004/0086556 A1 * | 5/2004 | Luo et al. ...................... 424/449 |
| 2004/0202710 A1 | 10/2004 | Muller |
| 2004/0210280 A1 | 10/2004 | Liedtke et al. |
| 2004/0241218 A1 * | 12/2004 | Tavares et al. ................ 424/449 |
| 2006/0084942 A1 | 4/2006 | Kim et al. |
| 2006/0210615 A1 | 9/2006 | Theobald et al. |
| 2007/0031463 A1 | 2/2007 | Fotinos et al. |
| 2007/0166233 A1 * | 7/2007 | Royds .......................... 424/10.2 |

FOREIGN PATENT DOCUMENTS

| DE | 19958554 | 1/2001 |
| DE | 10157124 | 5/2003 |
| EP | 0227836 | 7/1987 |
| EP | 0 413 034 | 2/1991 |
| EP | 0413034 | 2/1991 |
| EP | 0543241 | 5/1993 |
| JP | 2004168734 | 6/2004 |
| WO | WO2005/016320 | 2/2005 |
| WO | WO 2005/016320 | 2/2005 |

OTHER PUBLICATIONS

International Preliminary Report on Patentability.
International Preliminary Report on Patentability, Mar. 26, 2009.

* cited by examiner

*Primary Examiner* — Richard Schnizer
*Assistant Examiner* — Alma Pipic
(74) *Attorney, Agent, or Firm* — Frommer Lawrence & Haug

(57) ABSTRACT

The invention relates to a transdermal therapeutic system for applying an active ingredient or several active ingredients to the skin. Elongate hollow bodies are incorporated into one of the layers of the TTS, said hollow bodies containing a filling medium or several filling mediums. The invention also relates to the production and use of said type of systems.

21 Claims, No Drawings

TRANSDERMAL THERAPEUTIC SYSTEM CONTAINING ELONGATE HOLLOW BODIES

The present invention relates to a transdermal therapeutic system (TTS) for the application of an active substance or several active substances or a therapeutically effective salt thereof on the skin, wherein elongated hollow bodies, which have a filler or several fillers, are incorporated in the TTS. It further relates to the production and use of said systems.

Filled hollow fibers are used as reserve lubricants in cutting or grinding tools or, by releasing liquid adhesives, are used for removing hairline cracks in plastics. It is now technically possible to adapt the physical properties of elongated hollow bodies to the specific application. The range of properties then extends e.g. from glasslike brittle to flexible with rubberlike elasticity, from gas-tight to highly permeable. The outside diameter of elongated hollow bodies can range from less than 10 nm (nanotubes) up to several 100 μm (hollow fibers).

Hollow fibers are already used in TTS in the prior art. Thus, EP 0 227 836 A1 discloses a pharmaceutical preparation, comprising a pressure-sensitive adhesive film with hollow fibers, which have radially arranged pores. In this case the active substances can either be incorporated in the hollow fibers themselves, or alternatively the hollow fibers are empty and the active substance passes, by diffusion, through a layer of hollow fibers, to reach the surface of the skin. In this application hollow fibers are used with the function of a controlling membrane, or they bring about slow, controlled release of the active substance.

JP 2004-168734 discloses a nicotine patch for releasing nicotine, using hollow fibers with open pores, filled with a mixture of nicotine and a low-molecular substance. This slows down the release of the active substance from the TTS.

In EP 0 413 034 A1, a tissue-like composite of hollow fibers with open pores is used as a nonocclusive backing of a TTS, to reduce the accumulation of moisture in the TTS, which arises through transepidermal water loss, and thus improve the stability of the system during the period of use.

The problem to be solved by the present invention was to provide a transdermal therapeutic system (TTS), whose simple construction ensures, on the one hand, that the TTS can be stored safely and inactivation or activation of the system does not already occur during storage. On the other hand the invention should make it possible to activate or to deactivate the system—depending on the embodiment—at any point of time (before, after or during use) intentionally (actively) or automatically (passively).

This problem is solved superbly by a TTS as claimed in claim 1. Supply of radiant energy or other energy produces a change in structure of the hollow bodies, by which the filler or fillers are released from the hollow bodies. The energy can be supplied as mechanical, thermal, electrical, magnetic, electromagnetic or chemical energy. This depends on the particular properties of the hollow bodies. Preferably the energy is supplied in the form of pressure, heat, radiation, electric current or sound.

For example, brittle hollow bodies are subjected to mechanical stress by bending, extending, stretching, twisting or folding, so that they are deformed irreversibly. Through breakage or bursting of the structure of the hollow bodies in the TTS, the filler or several fillers are released from the elongated hollow bodies and can—depending on the particular embodiment—react in various ways. The degree of mechanical loading and therefore the start of breakage or bursting of the hollow tubes depends on the particular application and on the material of the hollow tubes. Thus, it is possible, for example, for a TTS to be folded actively before use, in order to activate it. In another embodiment, on removing the TTS from the skin there is, at least automatically, such severe bending that the hollow tubes used specifically for this application break, and the filler that is released, for example unused active substance, is inactivated. In accordance with DIN EN 28510, the hollow fibers are broken when the TTS is pulled away, e.g. from the skin or a substrate, at an angle of 180°, preferably >90°. Also, during use on the skin, by pressing on the TTS with a finger or another object, (pressure-sensitive) breaking can be achieved, so that activation takes place.

The principle described above is not operative in the case of flexible hollow tubes. Instead, other forms of energy, for example sound, heat, radiation etc., can be used as an effective means for breaking, bursting, disintegrating or perforating the hollow bodies. In a preferred embodiment, an additional agent is incorporated in the hollow bodies, which expands on supplying heat to the TTS, so that the hollow bodies burst. In another preferred embodiment, owing to their material properties the hollow bodies disintegrate or are perforated at temperatures above body temperature. A combination of brittle and flexible hollow tubes with different material properties is also preferred. In this way the active substances contained in the hollow bodies can for example be activated at defined points of time.

In a preferred embodiment the filler comprises at least one active substance and the release of the active substance or active substances takes place by breaking, disintegrating or perforating the hollow bodies. The separation of active substances and/or excipients in the matrix by the hollow tubes offers many advantages, which are explained in more detail below on the basis of examples, without limiting the invention to these. These examples only have the purpose of explaining the invention.

Therapeutic systems (TTS) are basically known by a person skilled in the art. Usually a TTS comprises a backing that is impermeable to the active substance, one or more layers containing the active substance, optionally a membrane controlling the release of the active substance and a detachable protective layer. If the layer containing the active substance(s) is in the form of a matrix layer, it can be of a self-adhesive form or can be provided additionally with a pressure-sensitive adhesive layer on the side next to the skin. In the case of a reservoir of active substance, the filler can be in the form of solution, suspension, gel or dispersion in a solid polymer matrix. A membrane controlling the release of the active substance is then inserted between the skin and the active substance reservoir, the membrane once again being provided with a pressure-sensitive adhesive layer on the side next to the skin, for fixing on the skin. Microreservoir systems, which contain the active substance in microencapsulated form, are also suitable. The layer containing the active substance(s) in the sense of the invention comprises at least one or more active substances and the elongated hollow bodies with filler, and the active substance or substances can be both inside and outside of the hollow bodies. The filler is in gaseous, liquid, semisolid or solid form. The system can be in the form of a multilayer system, with identical or different active substances in the various layers, or can also be at different concentrations. Active substance patches according to the invention, where after application on the skin the resultant TTS are transparent or at least translucent, are preferred.

The backing layer must be impermeable to the active substance contained in the TTS, to prevent undesirable escape of the active substance. Suitable backing materials are in particular polyesters, such as preferably polyethylene terephthalate (PET) and polybutylene terephthalate, which are particularly strong. Furthermore, almost any other compatible plastics are suitable, for example polyvinyl chloride, ethylene vinyl acetate, vinyl acetate, polyethylene, polypropylene, cellulose derivatives or combinations of various films. Composite laminates of aluminum and plastics such as polyethylene terephthalate are often used. The advantage of these composite laminates is that aluminum foil can be produced cheaply and is impermeable to nearly all pharmaceutical active substances. In addition, aluminum foil is opaque, which especially in the case of light-sensitive active substances offers the advantage of reliable protection from light.

Microporous polymer films produced with defined pore size from polyethylene, polypropylene, polyurethane, copolymers of ethylene and vinyl acetate (EVA) and silicones can be used as the controlling membrane. These polymer films are suitable if they are resistant to the substances contained in the preparation of active substance.

Suitable adhesives are high-viscosity substances, which stick to the skin after brief light pressure, so-called pressure-sensitive adhesives (PSA). They possess high strength of cohesion and adhesion. Pressure-sensitive adhesives based on poly(meth)acrylates, based on polyisobutylenes and based on silicones are used. The layer of pressure-sensitive adhesive can contain active substance(s) or can be without active substance(s). In the sense of the invention the layer of pressure-sensitive adhesive can be the layer containing the active substance(s) and therefore also include the elongated hollow bodies. The active substance or active substances can therefore be present only in the layer or only in the elongated hollow bodies. The active substances can also, however, be present both in the layer and in the elongated hollow bodies.

The pressure-sensitive adhesive layer and/or optionally present reservoir or matrix layer(s) of the TTS according to the invention can comprise a material that is selected from the group comprising pressure-sensitive adhesive polymers based on acrylic acid and/or methacrylic acid and esters thereof, polyacrylates, isobutylene, polyvinyl acetate, ethylene-vinyl acetate, natural and/or synthetic rubbers, for example acrylonitrile-butadiene rubber, butyl rubber or neoprene rubber, styrene-diene copolymers such as styrene-butadiene block copolymers and hotmelt adhesives, or that is produced on the basis of pressure-sensitive adhesive silicone polymers or polysiloxanes.

Polyacrylates are generally produced by polymerization of various monomers (at least one monomer from the group comprising acrylic acid, methacrylic acid, acrylic acid esters and methacrylic acid esters) and in particular from mixtures thereof. Preferably organic solvents, in some cases even water, are preferably used as solvent during polymerization for the production of a suitable polyacrylate. Depending on the structure of the monomers used in the polymerization, polyacrylates are obtained that can contain functional groups. Polyacrylates with OH groups (hydroxyl groups) and those with COOH groups (carboxyl groups) as functional groups are widely used.

Silicones, polysiloxanes or silicones, which can themselves be pressure-sensitive adhesives, find application as suitable silicone polymers. Silicone pressure-sensitive adhesives are taken to mean pressure-sensitive adhesives based for example on a polydimethylsiloxane structure or polydimethyl-diphenylsiloxane structure. In particular, commercially available silicone pressure-sensitive adhesives, for example BIO-PSA from Dow Corning Corporation, are suitable.

The protective layer serves for protection of the layer, next to the skin, of pressure-sensitive adhesive of the patch during storage and is removed shortly before use.

Generally this comprises films provided with adhesive, for example polyester films of polyethylene terephthalate (PET), siliconized on one side.

All active substances that are suitable for transdermal or topical application may be considered as active substances. These include, in the sense of the invention, chemical substances, pharmaceuticals, odorants, and pheromones. The active substance or active substances can also be in the form of their pharmacologically active salts or as a prodrug. A prodrug is a substance which, without being metabolized, is pharmacologically inactive or slightly active, and is only transformed to a fully active substance following metabolization in the body.

In a special embodiment, the sensitive and/or highly volatile active substances are contained in the elongated hollow bodies. As a result the risk of loss of the active substance before use owing to diffusion processes is prevented, or at least greatly reduced. As already described, the active substances can be present in various layers, the elongated hollow bodies being contained in at least one of the layers. The active substance is preferably an active substance from the analgesics group, e.g. narcotics. We may preferably mention morphine derivatives, heroin and buprenorphine, or fentanyl, sufentanil and alfentanil or derivatives thereof. Sensitive and/or highly volatile active substances are also preferably used, for example nicotine, nitroglycerin, salicylic acid, scopolamine, benzatropine, bupropion, cyclopentamine dapsaicin, fenfluramine, fentanyl, cyclopentamine, ephedrine, selegiline, sufentanil, oxybutynin, rasagiline, mecamylamine, memantine, methylsalicylate, venlafaxine, and others.

The layer containing the active substance(s) can, in addition to the active substance or active substances and the elongated hollow bodies, additionally contain other excipients, such as plasticizers, tackifiers, solubilizers, stabilizers, fillers, carriers, permeation accelerators, for example fatty alcohols, polyol fatty acid esters, polyalcohols, Azone, alkylmethylsulfoxides, pyrrolidone, nonionic surfactants, anionic surfactants, cationic surfactants, and terpenes, which basically are known by a person skilled in the art. Other preferred excipients in the present invention are e.g. silicone oil, glycerol esters of hydrogenated resin acids, hydroabietine-alcohol-resin esters, hydroabietine-acid-resin esters, hydrogenated methyl esters of pine resins, esters of partially hydrogenated pine resins, esters of pine resins, colophony, phenolic resin, alkylphenolic resin, petroleum resin, xylene resin. Alternatively, antioxidants can additionally be used, such as tocopherols, butylated hydroxyanisole (BHA), gallic acid esters, butylated hydroxytoluene (BHT), ascorbyl palmitate, ascorbyl stearate, for stabilization or to minimize degradation of the active substance(s) during storage. The preparation of active substance(s) can additionally contain viscosity-increasing excipients, which do not have any release-controlling function. Preferably the viscosity-increasing excipient is selected from the group comprising finely-divided silicon dioxide, for example Aerosil R 974®, metal oxides, titanium oxide, zinc oxide, silicate, aluminum and magnesium silicate, talc, stearate, zinc stearate, polyethylene, polystyrene-insoluble polyvinylpyrrolidone, polyacrylic acids, e.g. Carbopol 934P®, mineral oils, wool waxes and high-molecular polyethylene glycols. An example of a preferred polyethylene glycol is Carbowax 1000®. By adding suitable solvents, and optionally further excipients, it is possible to adjust the viscosity of the preparation of active substance(s). In principle, all common organic solvents are suitable as solvents, for example ethanol, isopropyl alcohol, hexane, heptane, ethyl acetate, petroleum ether, gasoline, ketones, acetone, glycerol, DEET (N,N-diethyl-3-methylbenzamide), THF and many oils, for example silicone oil, paraffin, triglycerides, neutral oil or vegetable oils. For better dissolution of the active substance in the polymer, the transdermal therapeutic systems can contain one or more solvents. Soluble polyvinylpyrrolidone, Kollidon-vinyl acetate, propylene glycol, ethyl oleate, 1,2-propanediol, 1,3-butanediol, transcutol, propylene glycol monocaprylate, solketal, oleic acid, 1-methylpyrrolidone, glycerol, lauryllactate, triacetin, glycerol monooleate, sorbitan monooleate and sorbitan trioleate can be considered for this. Propylene glycol, butanediol and lauryllactate are especially preferred.

An elongated hollow body, in the sense of this application, means an object whose length is greater than its width. Typically they have a length of a few micrometers. However, hollow bodies up to 20 centimeters are already available. When hollow bodies are used in the form of flow cushions, pads or compresses, the products can even be up to several meters long. The outside diameter of the hollow bodies is from 1 nm to 1000 µm, preferably 10 nm to 500 µm, especially preferably 10 nm to 100 µm, quite especially preferably 10 nm to 50 µm. For example, hollow fibers, nanofibers, nanotubes, buckytubes, nano-scale carbon tubes, carbon nanotubes (CNTs) are used.

The hollow bodies can be single-walled or multiwalled, with the wall forming a closed ring or a spiral structure, where the cross-section remains largely the same over the length of the hollow bodies and is preferably circular. The wall thickness depends on the manner of production and is preferably in the range from 5 to 10% of the outside diameter. Preferably they are not provided with pores and so can be regarded as impermeable to the filler. One or more fillers are provided in the hollow bodies, for example a gas or a mixture of various gases, a liquid or several liquids (solutions, suspensions, emulsions), a solid or several solids or a semisolid preparation (pastes, gels, ointments, creams, etc.). In the preferred embodiment the diameter is infinitesimally small relative to the length, therefore with regard to impermeability it is immaterial whether the ends of the hollow bodies are open.

The preferred hollow bodies can only be deformed plastically to a predetermined extent—depending on the embodiment—before cracks develop and the hollow bodies finally break. They therefore possess brittleness. They break at a predetermined bending radius or angle, which can be adjusted via the composition of the material forming the wall of the hollow bodies, e.g. when pulling the TTS off of the skin or through pressure of a finger or some other object on the TTS located on the skin. In this way a (pressure-sensitive) breaking is achieved, and activation or deactivation of the system is started. However, other possibilities, for example sound, heat, radiation etc., can also be used as effective means for disrupting the hollow bodies. In such an embodiment the mechanical properties of the hollow fibers can be conceived as being in the complete range from glasslike brittle to rubberlike elastic.

No limits are placed on the choice of materials. Usually they consist of carbon, metals, metal oxides or polymeric compounds or combinations thereof. The use of a new group of materials, the ORMOCER®s, in which glasslike components are combined with polymeric components, is especially preferred. The composite material consists of an inorganic silicon-oxygen network in which special organic crosslinkable groups of molecules are incorporated. The inorganic, glasslike structures make spinning of the material possible. The organic segments ensure that the properties of the fibers can be modified without any problem. Thus, the spectrum of properties of the ORMOCER® hollow fibers extends from glasslike-brittle to flexible with rubberlike elasticity, and from gas-tight to highly permeable. In a special embodiment, the layer containing the active substance(s) comprises, as well as the brittle hollow bodies, in addition flexible hollow bodies. These can be activated using sound, heat or radiation as the triggering principle, so that they release their contents.

Production of hollow fibers takes place by techniques that are known by a person skilled in the art, e.g. by spinning processes, in which a resin is forced through a hollow spinning nozzle by compressed air. Then the fiber is cured with UV radiation. Other processes are for example electrospinning, in which a high voltage is applied to a nozzle through which a polymer solution or melt is pumped, the TUFT process (Tubes by Fiber Templates), which is based on the coating of template fibers with selective removal of the template after the hollow bodies have formed, or the WASTE process (Wetting Assisted Templating) in which the walls of the pores in a porous template are wetted with a polymer solution or melt. Then the hollow bodies thus obtained can be further functionalized by selective introduction of functional groups on the inside or outside wall of the hollow bodies.

The elongated hollow bodies thus produced can either be incorporated just as loose material in the TTS or, as whole bundles, can be processed into threads or mats and then used as flat layers, as films, as laminates or fabrics, woven sheet-like pads, e.g. as flat-shaped, e.g. woven material from filled elongated hollow bodies in ribbon or roll form, from which the contour to be used is obtained in a combined sealing and/or punching process, without the filler escaping from the elongated hollow bodies.

as film-shaped material, in which the filled elongated hollow bodies are embedded in a carrier medium, e.g. of plastic such as polyurethane.

as flat layers of filled elongated hollow bodies (pads) with defined dimensions between 0.1 and 200 cm$^2$.

The varied techniques of TTS production that are sufficiently well known by a person skilled in the art are available for incorporating the hollow bodies in the form of said flat layers. The filled elongated hollow bodies are embedded in the TTS in the form of a loose material, by direct inclusion in the coating compound before the coating process direct inclusion in the active substance reservoir before the coating process application of the loose material on the adhesive matrix before it has dried application of the loose material on the dried adhesive matrix Before the laminate is covered with the backing, the layer of hollow bodies can be covered with one or more additional layers.

In the simplest case the filler is an active substance, which is contained in the elongated hollow bodies. By folding or twisting the TTS, the hollow bodies are broken and the active substance is released from the hollow bodies. This construction ensures reliable storage. However, release can also be effected by disintegrating or perforating the hollow bodies, but depends on the properties of the hollow bodies. With the construction of the TTS provided, in fact the system is specially activated before use. This embodiment is especially advantageous in the case of sensitive or highly volatile active substances, in particular nicotine, or if there is incompatibility with another ingredient of the system. Examples of said active substances are in particular nicotine, nitroglycerin, salicylic acid, scopolamine, benzatropine, fenfluramine, cyclopentamine, ephedrine, selegiline, rasagiline, mecamylamine, memantine and others.

Usually in cases of misuse, an attempt is made to reach the analgesic active substance by extraction of TTS that are worn. In a special embodiment, the object of the invention lowers the potential for misuse of opioid-containing analgesic patches considerably. In this embodiment the active substance is contained in the matrix and the hollow bodies contain, as filler, a substance that destroys or inactivates the active substance on contact. Now if the TTS is removed from the skin, the pulling and the associated high level of mechanical stress (bending) of the TTS causes the hollow bodies to break. The substance is released and comes in contact with the active substance. This is for example destroyed irreversibly by oxidative processes or is inactivated by release of an antagonist. Suitable oxidizing agents are in particular inorganic reagents, such as permanganates, e.g. potassium permanganate, manganese dioxide, lead dioxide, lead tetraacetate, cerium(IV) salts, chromates, chromic acid, osmium tetroxide, nitric acid, nitrites, such as potassium nitrite, selenium dioxide, hydrogen peroxide and other peroxo compounds, bromine, chlorine, hypohalides, or sulfur; preferably potassium permanganate, hydrogen peroxide and potassium nitrite; organic oxidizing agents, such as dimethylsulfoxide, N-bromosuccinimide, quinones, hypervalent iodine compounds, peracids and peresters, as well as enzymes. For a given active substance, the oxidizing agent is preferably selected based on its chemical reactivity with the active substance. Abusive isolation of the active substance is therefore effectively prevented. The active substance is preferably an active substance from the analgesics group, for example narcotics. We may preferably mention morphine derivatives, heroin and buprenorphine, or fentanyl and its derivatives sufentanil and alfentanil. Basically, combinations of active substances can also be used, for which application via a TTS is the appropriate dosage form.

In another preferred embodiment the matrix layer containing the active substance(s) has at least two active substances, with at least one of the active substances located in the elongated hollow bodies. This division is of advantage when there are at least two active substances that are not compatible with each other and should not come into contact until shortly before use. A special advantage that follows from this construction is that the breaking, disintegrating or perforating of the hollow bodies preferably does not take place until after a given time interval, e.g. after 6 to 36 or up to 168 hours, and then the active substance is released with a time delay relative to the first. We therefore have a two-phase TTS for application twice, with simultaneous use of the same TTS for the repeated use. After the first wearing period, the second phase of the TTS is started by breaking of the hollow bodies (by the user) on the skin or after removal of the TTS and reattachment of the TTS.

In another preferred embodiment, in the layer containing the active substance(s) there is at least one active substance in the form of one of its pharmacologically active salts. In the elongated hollow bodies there is, as filler, a basic excipient, which releases the active substance from the salt form and thus converts it into the pharmacologically active or more active form. This preferred embodiment of the invention is therefore the in-situ production of an active-substance base by release by the basic excipient before using the TTS. The opposite arrangement (active substance in the salt form as filler in the elongated hollow bodies and basic excipient in the layer) is also a preferred embodiment of this invention.

In another especially preferred embodiment, the walls of the elongated hollow bodies are designed to be semipermeable. Water in the form of moisture on the skin can therefore be absorbed into the hollow bodies during the period of use of the TTS. Supply of water into the hollow bodies by diffusion of solvent through the semipermeable membrane causes the hollow bodies to expand to such an extent that they burst and release the filler. In addition, hollow bodies not filled semipermeably can also be present in the TTS, which advantageously prevent or at least reduce any decrease in strength of adhesion of the TTS or degradation of the active substance during the period of use owing to transepidermal water loss from the skin.

The invention claimed is:

1. A transdermal therapeutic system (TTS) for delivering an active substance or more than one active substances, the transdermal therapeutic system comprising:
   a backing that is impermeable to the active substance(s);
   a layer containing the active substance(s) or several layers containing the active substance(s); and
   optionally a detachable protective layer;
   wherein at least one layer containing the active substance(s) has physically distinct elongated hollow bodies each with a hollow space provided with a filler or several fillers, where the hollow space of each hollow body is noncontiguous with the hollow space of each other hollow body;
   wherein the elongated hollow bodies are configured so that the filler or fillers are only released from the hollow bodies by changing the structure of the hollow bodies; and
   wherein the elongated hollow bodies are incorporated in the at least one layer in the form of loose materials, and include at least one selected from the group consisting of hollow fibers, nanofibers, nanotubes, buckytubes, nanoscale carbon tubes, and carbon nanotubes.

2. The transdermal therapeutic system as claimed in claim 1;
   wherein the change in structure of the hollow bodies is brought about by supplying mechanical, thermal, electrical, magnetic, electromagnetic or chemical energy.

3. The transdermal therapeutic system as claimed in claim 1;
   wherein the change in structure of the hollow bodies is caused by pressure, heat, radiation, electric current or sound.

4. The transdermal therapeutic system as claimed in claim 1;
   wherein the filler comprises at least one active substance and the release of the active substance or active substances is effected by breaking, disintegrating or perforating the hollow bodies.

5. The transdermal therapeutic system as claimed in claim 1;
   wherein the layer containing the active substance(s) contains at least two active substances;
   wherein at least one of the active substances is located in the elongated hollow bodies; and
   wherein the elongated hollow bodies are configured to release the at least one active substance by breaking, disintegrating, or perforating the hollow bodies.

6. The transdermal therapeutic system as claimed in claim 1;
   wherein the filler contained in the hollow bodies has the property of inactivating the active substance or active substances.

7. The transdermal therapeutic system as claimed in claim 1;
   wherein the filler contained in the hollow bodies has the property of destroying the active substance or active substances.

8. The transdermal therapeutic system as claimed in claim 6;
  wherein the filler is only released from the hollow bodies by mechanical stressing of the TTS during removal of the TTS from skin to which it has been attached.

9. The transdermal therapeutic system as claimed in claim 1;
  wherein the layer containing the active substance(s) contains at least one active substance in the form of one of its therapeutically effective salts; and
  wherein an excipient that releases the active substance from the salt form is contained in the hollow bodies.

10. The transdermal therapeutic system as claimed in claim 1;
  wherein the layer containing the active substance(s) contains at least one active substance in the form of one of its therapeutically effective salts; and;
  wherein the layer containing the active substance(s) contains an excipient that releases the active substance from the salt form, with the at least one active substance in the form of one of its therapeutically effective salts being located in the hollow bodies.

11. The transdermal therapeutic system as claimed in claim 1;
  wherein the wall of the hollow bodies is designed to be semipermeable.

12. The transdermal therapeutic system as claimed in claim 1;
  wherein the outside diameter of the hollow bodies is from 1 nm to 1000 µm.

13. The transdermal therapeutic system as claimed in claim 1;
  wherein the hollow bodies are designed to be brittle or flexible.

14. The transdermal therapeutic system as claimed in claim 1;
  wherein the hollow bodies are made from organically modified ceramic polymer hollow fibers.

15. The transdermal therapeutic system as claimed in claim 1;
  wherein the layer containing the active substance(s) additionally has a pressure-sensitive adhesive layer on a skin-facing side.

16. The transdermal therapeutic system as claimed in claim 1;
  wherein the change in structure of the hollow bodies is caused by heat.

17. The transdermal therapeutic system as claimed in claim 16;
  wherein the walls of the hollow bodies are designed to be semipermeable.

18. The transdermal therapeutic system as claimed in claim 17;
  wherein the outside diameter of the hollow bodies is from 10 nm to 50 µm.

19. The transdermal therapeutic system as claimed in claim 18;
  wherein the filler of the hollow bodies includes an antagonist.

20. The transdermal therapeutic system as claimed in claim 18;
  wherein the filler includes an oxidizing agent.

21. The transdermal therapeutic system as claimed in claim 1;
  wherein the outside diameter of the hollow bodies is from 1 nm to less than 10 µm.

* * * * *